US010426653B2

(12) United States Patent
Will et al.

(10) Patent No.: US 10,426,653 B2
(45) Date of Patent: Oct. 1, 2019

(54) ARM IMMOBILIZATION APPARATUS

(71) Applicants: David M. Will, New Albany, OH (US); Christin F. Will, New Albany, OH (US)

(72) Inventors: David M. Will, New Albany, OH (US); Christin F. Will, New Albany, OH (US)

(*) Notice: Subject to any disclaimer, the term of this patent is extended or adjusted under 35 U.S.C. 154(b) by 1102 days.

(21) Appl. No.: 14/339,227

(22) Filed: Jul. 23, 2014

(65) Prior Publication Data

US 2016/0022469 A1 Jan. 28, 2016

(51) Int. Cl.
*A61F 5/00* (2006.01)
*A61F 5/37* (2006.01)

(52) U.S. Cl.
CPC .................. *A61F 5/3723* (2013.01)

(58) Field of Classification Search
CPC .. A61F 5/0118; A61F 5/05858; A61F 5/3723; A61F 5/373; A61F 5/3738; A61F 5/3746; A61F 5/3753; A61H 1/0277; A61H 1/0281; A41D 13/02; A41D 15/04; A47G 9/083; A41B 13/005; A41B 13/00; A41B 13/10; A41B 13/103; A41B 13/06; A41B 13/065
USPC .... 602/4, 5, 19, 20; 2/69, 69.5, 88, 89, 461, 2/459, 80, 83, 46, 104
See application file for complete search history.

(56) References Cited

U.S. PATENT DOCUMENTS

| 1,266,688 | A | * | 5/1918 | Kassner | A61F 5/3738 602/4 |
| 1,621,323 | A | * | 3/1927 | Horn | A61F 5/3746 2/92 |
| 2,576,812 | A | * | 11/1951 | Siegel | A41B 13/00 2/80 |
| 5,129,406 | A | | 7/1992 | Magnusen et al. | |
| 5,358,470 | A | * | 10/1994 | Johnson | A61F 5/3746 128/DIG. 15 |
| 5,651,143 | A | * | 7/1997 | Zehrung | A47D 13/025 2/16 |
| 6,110,133 | A | | 8/2000 | Ritts | |
| 6,595,936 | B1 | * | 7/2003 | Oladipo | A61F 5/3746 602/20 |
| 6,935,342 | B2 | * | 8/2005 | Larson | A61F 5/3723 119/770 |
| 6,979,303 | B2 | * | 12/2005 | Jestrabek-Hart | A61F 5/3738 2/45 |
| 8,973,793 | B2 | * | 3/2015 | Arvan | A47D 13/02 224/158 |

(Continued)

OTHER PUBLICATIONS

International Search Report and Written Opinion dated Oct. 7, 2015 for related PCT Application No. PCT/US2015/039474 filed Jul. 8, 2015.

*Primary Examiner* — Keri J Nelson
*Assistant Examiner* — Adam Baker
(74) *Attorney, Agent, or Firm* — Benesch, Friedlander, Coplan & Aronoff LLP (57) ABSTRACT

An arm immobilization apparatus may at least partially envelope both a patient's torso and the patient's injured arm. The apparatus may include a front flap configured to cover the injured arm and secure it against the patient's torso using at least one fastening device. The apparatus may at least partially prevent patients with less than fully developed, or reduced, mental capacity, from moving the injured arm.

15 Claims, 7 Drawing Sheets

(56) References Cited

U.S. PATENT DOCUMENTS

| | | | |
|---|---|---|---|
| 2002/0068892 A1* | 6/2002 | Estep | A61F 5/3746 602/60 |
| 2005/0015033 A1* | 1/2005 | Moore | A61F 5/3746 602/4 |
| 2010/0125930 A1* | 5/2010 | Burrell, IV | A41B 13/08 2/75 |
| 2012/0125347 A1* | 5/2012 | Soileau | A41B 13/06 128/873 |
| 2012/0209159 A1 | 8/2012 | Fout | |
| 2013/0237893 A1 | 9/2013 | Knox | |

* cited by examiner

ARM IMMOBILIZATION APPARATUS

BACKGROUND

When a human sustains an injury to, or disease of, his or her arm, it may be common to stabilize the injured arm to permit it to properly heal. Such practice may be a result of the human body's natural response to injury, wherein blood flows to the damaged tissue to help prevent movement of the injured body part. This phenomena may commonly be known as swelling. Furthermore, the injury may result in pain, which may discourage many humans from attempting to move or otherwise use the injured body part.

However, every person may not respond to pain in the same way. Moreover, some people may not feel pain when injured, while some injuries may not induce pain. Some people may feel pain, but not associate the pain with the injury. People with less than fully developed, or reduced, mental capacity may be especially susceptible to such dissociation with injury, pain, and the desire to refrain from moving or otherwise using an injured body part.

Less than fully developed, or reduced, mental capacity may be a result of many factors, including without limitation, underdevelopment of the mental faculties, physical trauma, chemical imbalance, and disease. Common examples of people with less than fully developed, or reduced, mental capacity may include, without limitation, infants, head trauma victims, and individuals with intellectual disabilities (also known as mental retardation).

People with less than fully developed, or reduced, mental capacity may be at a greater risk or re-injury due to their inability to self-regulate the movement or use of their injured body parts. Furthermore, less than fully developed, or reduced, mental capacity may preclude such people from understanding instructions provided to them by medical professionals. For example, an infant may not understand that he or she should not move an injured body part, and the infant may not understand directions instructing him or her to keep the injured body part immobilized.

Devices have been developed that may aid patients in immobilizing their injured or diseased body parts. A common example is the triangular sling, which may be donned by a patient to immobilize an injured arm. A triangular sling wraps around the lower arm at one end, wraps around the neck at the other end, and is used to support the weight of the injured arm. However, a triangular sling may support the arm in the vertical axis only, and specifically, only in a direction opposite the force caused by the acceleration of gravity acting upon the mass of the injured arm. A triangular sling may thus provide little to no support horizontally, radially, or in a downward vertical direction. As a result, a patient who does not understand the importance of keeping the arm immobilized is not prevented by the triangular sling from moving the injured arm in these unrestrained directions. A patient who is permitted to move an injured body part may be more likely to either re-injure or slow the healing process of the injured body part.

Another possible cause of the unrestrained mobility of an injured arm supported by a triangular sling is the relative ease with which the triangular sling may be removed. For example, a triangular sling merely rests around the neck of the patient, with nothing but friction and the weight of the injured arm holding it in place. Likewise, the distal end of the triangular sling merely rests around the lower arm of the patient, with nothing but friction and the weight of the injured arm holding the triangular sling in place. It may take little effort to remove a triangular sling donned in this manner. Furthermore, such a sling may inadvertently be disrupted such that it may no longer properly support and immobilize the injured arm.

Thus, an injured or diseased arm may need to be properly immobilized, despite a patient's potential inability to willfully maintain such immobilization. What is needed is an apparatus to more securely and/or reliably immobilize a patient's arm.

SUMMARY

In one embodiment, an apparatus for immobilizing an injured arm of a patient is provided, the apparatus comprising: an anterior portion having an inferior portion and a superior portion; a posterior portion having an inferior portion and a superior portion; wherein the anterior portion is joined to the posterior portion at one or more of the left side, right side, left shoulder, and right shoulder of the patient, wherein at least one of the anterior portion and the posterior portion cover at least a portion of the torso of the patient, wherein the posterior inferior portion is of sufficient length to extend distally about the pelvis (between a left leg and a right leg) of the patient and overlap or underlap with at least a portion of the anterior inferior portion, wherein at least one of the anterior inferior portion and the posterior inferior portion include at least one fastening device, an anterior flap having a proximal end and a distal end, wherein the proximal end of the anterior flap is affixed to the anterior portion at about the anterior torso of the patient, wherein the distal end of the anterior flap includes at least one fastening device, wherein the anterior flap is of sufficient length to permit the distal end of the anterior flap to be pulled at least one shoulder of the patient; a posterior flap having a proximal end and a distal end, wherein the proximal end of the posterior flap is affixed to the posterior portion at about the posterior torso of the patient, wherein the distal end of the posterior flap includes at least one fastening device, and wherein the posterior flap is of sufficient length to permit the distal end of the posterior flap to be pulled over at least one shoulder of the patient.

In another embodiment, an apparatus for immobilizing an injured arm of a patient is provided, the apparatus comprising: an anterior portion having an inferior portion and a superior portion; a posterior portion having an inferior portion and a superior portion; a left shoulder portion and a right shoulder portion; wherein the anterior portion is joined to the posterior portion at one or more of the left side, right side, left shoulder, and right shoulder of the patient, wherein at least one of the anterior portion and the posterior portion cover at least a portion of the torso of the patient, wherein the posterior inferior portion is of sufficient length to extend distally about the pelvis of the patient and meet, overlap, or underlap with at least a portion of the anterior inferior portion, wherein at least one of the anterior inferior portion and the posterior inferior portion include at least one fastening device, wherein at least one of the left shoulder portion and the right shoulder portion include at least one fastening device; an anterior flap having a proximal end and a distal end, wherein the proximal end of the anterior flap is affixed to the anterior portion at about the anterior torso of the patient, wherein the distal end of the anterior flap includes at least one fastening device, and wherein the anterior flap is of sufficient length to permit the distal end of the anterior flap to be pulled over at least one of the shoulders of the patient.

In one embodiment, a method for immobilizing an injured arm of a patient is provided, the method comprising: dressing a patient in an arm immobilization apparatus having: an anterior portion having an inferior portion and a superior portion; a posterior portion having an inferior portion and a superior portion; wherein the anterior portion is joined to the posterior portion at one or more of the left side, right side, left shoulder, and right shoulder of the patient, wherein at least one of the anterior portion and the posterior portion cover at least a portion of the torso of the patient, wherein the posterior inferior portion is of sufficient length to extend distally about the pelvis of the patient and meet, overlap, or underlap with at least a portion of the anterior inferior portion, wherein at least one of the anterior inferior portion and the posterior inferior portion include at least one fastening device, wherein the at least one fastening device is configured to permit the at least one fastening device of the anterior inferior portion to be operatively connected to the at least one fastening device of the posterior inferior portion when the posterior inferior portion is extended distally about the pelvis of the patient and oriented to overlap or underlap with at least a portion of the anterior inferior portion; an anterior flap having a proximal end and a distal end, wherein the proximal end of the anterior flap is affixed to the anterior portion at about the anterior torso of the patient, wherein the distal end of the anterior flap includes at least one fastening device, wherein the anterior flap is of sufficient length to permit the distal end of the anterior flap to be pulled over either shoulder of the patient; a posterior flap having a proximal end and a distal end, wherein the proximal end of the posterior flap is affixed to the posterior portion at about the posterior torso of the patient, wherein the distal end of the posterior flap includes at least one fastening device, wherein the posterior flap is of sufficient length to permit the distal end of the posterior flap to be pulled over at least one of the shoulders of the patient, wherein the at least one fastening device of the distal end of the anterior flap is configured to be operatively connected to the at least one fastening device of the distal end of the posterior flap at a position superior to at least one of the shoulders of the patient; positioning the distal end of the anterior flap in a position extended toward the feet of the patient; wherein the at least one fastening device of the distal end of the posterior flap is positioned superior and posterior to the opposite shoulder of the arm to be immobilized; placing the upper portion of the arm to be immobilized at about the side of the patient and the lower portion of the arm to be immobilized at an angle from the upper portion of the arm, wherein the arm of the patient is flexed at the elbow about 90° and adducted across the torso of the patient; orienting the distal end of the anterior flap over the arm to be immobilized; positioning the distal end of the anterior flap in a position extended toward the head of the patient, wherein the at least one fastening device of the distal end of the anterior flap is positioned superior to the opposite shoulder of the arm to be immobilized; and securing the at least one fastening device of the distal end of the anterior flap to the at least one fastening device of the distal end of the posterior flap, wherein the distal end of the anterior flap is secured to the distal end of the posterior flap at a position superior to the opposite shoulder of the immobilized arm of the patient.

BRIEF DESCRIPTION OF THE DRAWINGS

The accompanying figures, which are incorporated in and constitute a part of the specification, illustrate various example apparatuses and systems, and are used merely to illustrate various example embodiments. In the figures, like elements bear like reference numerals.

DETAILED DESCRIPTION

An apparatus may be used to immobilize the injured arm of a patient with less than fully developed, or reduced, mental capacity, or a patient who otherwise may not be relied upon to immobilize the injured or diseased arm. Such an arm immobilization apparatus may provide the patient with less freedom of movement about the torso and upper body appendages. This reduction in the patient's freedom of movement may be accomplished by at least partially enveloping the patient's torso in an arm immobilization apparatus that may be donned and secured around the injured arm without being easily and inadvertently or accidently removed. Such an arm immobilization apparatus may envelope the injured or diseased arm and secure it against the torso of the patient, thereby at least partially preventing the patient from moving the injured arm. Such an arm immobilization apparatus may be constructed from nearly any type of fabric commonly used to make clothing and other consumer goods, including without limitation, cotton, polyester, nylon, natural and synthetic fibers.

The apparatus may be used in immobilizing an injured limb, such as an arm, to aid in healing of the limb. The apparatus may be used in immobilizing a diseased limb, such as an arm, for therapeutic purposes.

Figure 1:
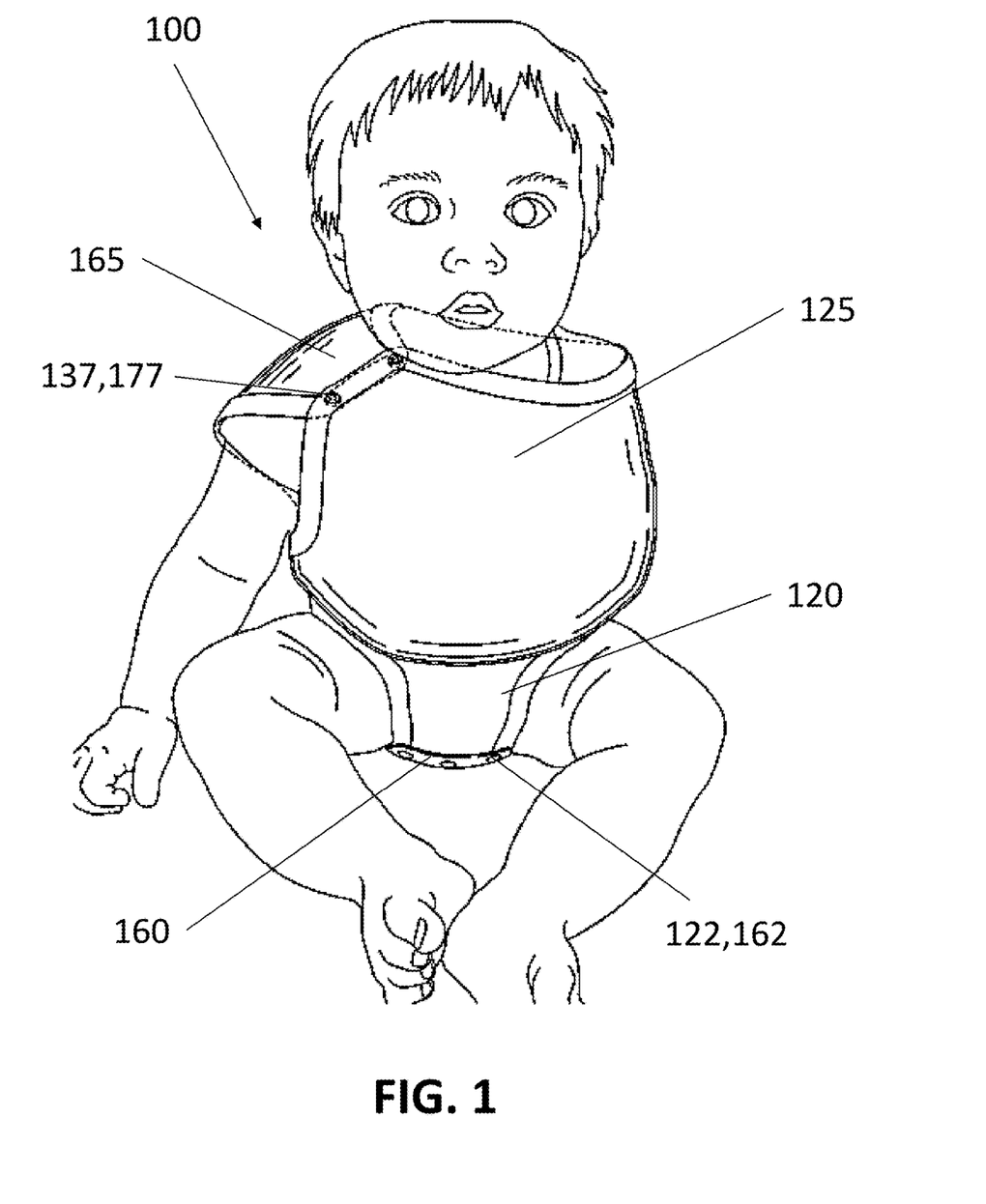
FIG. 1 illustrates a front elevational view of an example arrangement of an arm immobilization apparatus.

FIG. 1 illustrates a front elevational view of one example arrangement of arm immobilization apparatus 100 as worn by an infant. An anterior flap 125 may be oriented to at least partially enclose an injured arm (not shown).

Anterior flap 125 may be configured to be operatively connected to a posterior flap 165 at a position superior to the shoulder of the infant by at least one fastening device 137,177.

An anterior inferior portion 120 may be operatively connected to a posterior inferior portion 160 at a position inferior to the pelvis of the patient by at least one fastening device 122,162.

Figure 2:
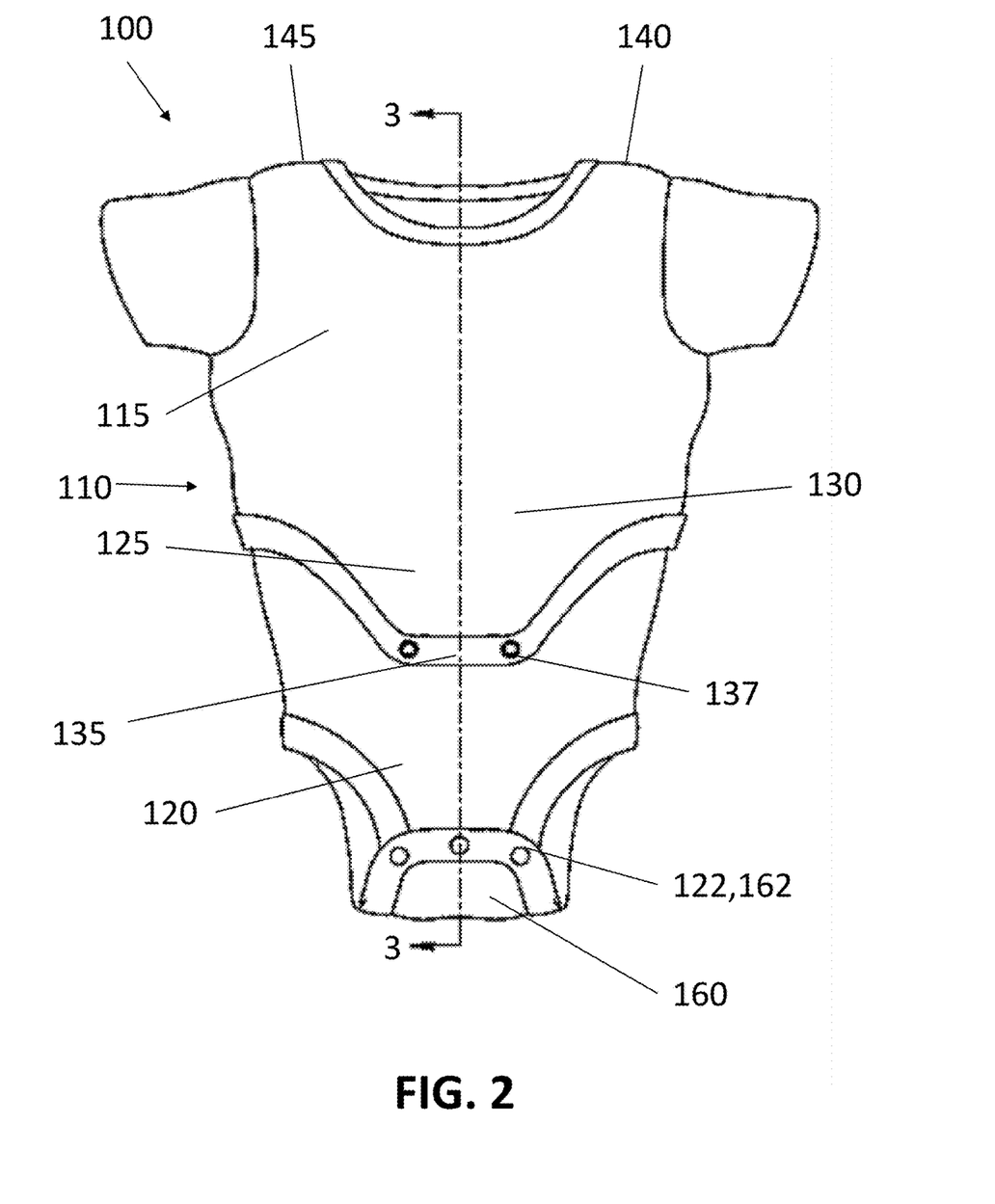
FIG. 2 illustrates a front elevational view of an example arrangement of an arm immobilization apparatus.

FIG. 2 illustrates a front elevational view of arm immobilization apparatus 100, which may include an anterior portion 110 having a superior portion 115 and inferior portion 120. Superior portion 115 and inferior portion 120 may be operatively connected. Superior portion 115 and inferior portion 120 may be integrally connected. Superior portion 115 and inferior portion 120 may be removably connected.

Anterior flap 125 may include a proximal end 130 and a distal end 135. Proximal end 130 of anterior flap 125 may be integrally, or removably, affixed to anterior portion 110 at about the anterior torso of the patient.

Distal end 135 of anterior flap 125 may include at least one fastening device 137. Anterior flap 125 may be of sufficient length to permit distal end 135 of anterior flap 125 to be pulled over either shoulder of the patient. Anterior flap 125 may be of sufficient length to permit distal end 135 of anterior flap 125 to be pulled over both shoulders of the patient.

Arm immobilization apparatus 100 may include left shoulder portion 140 and right shoulder portion 145.

Figure 3:
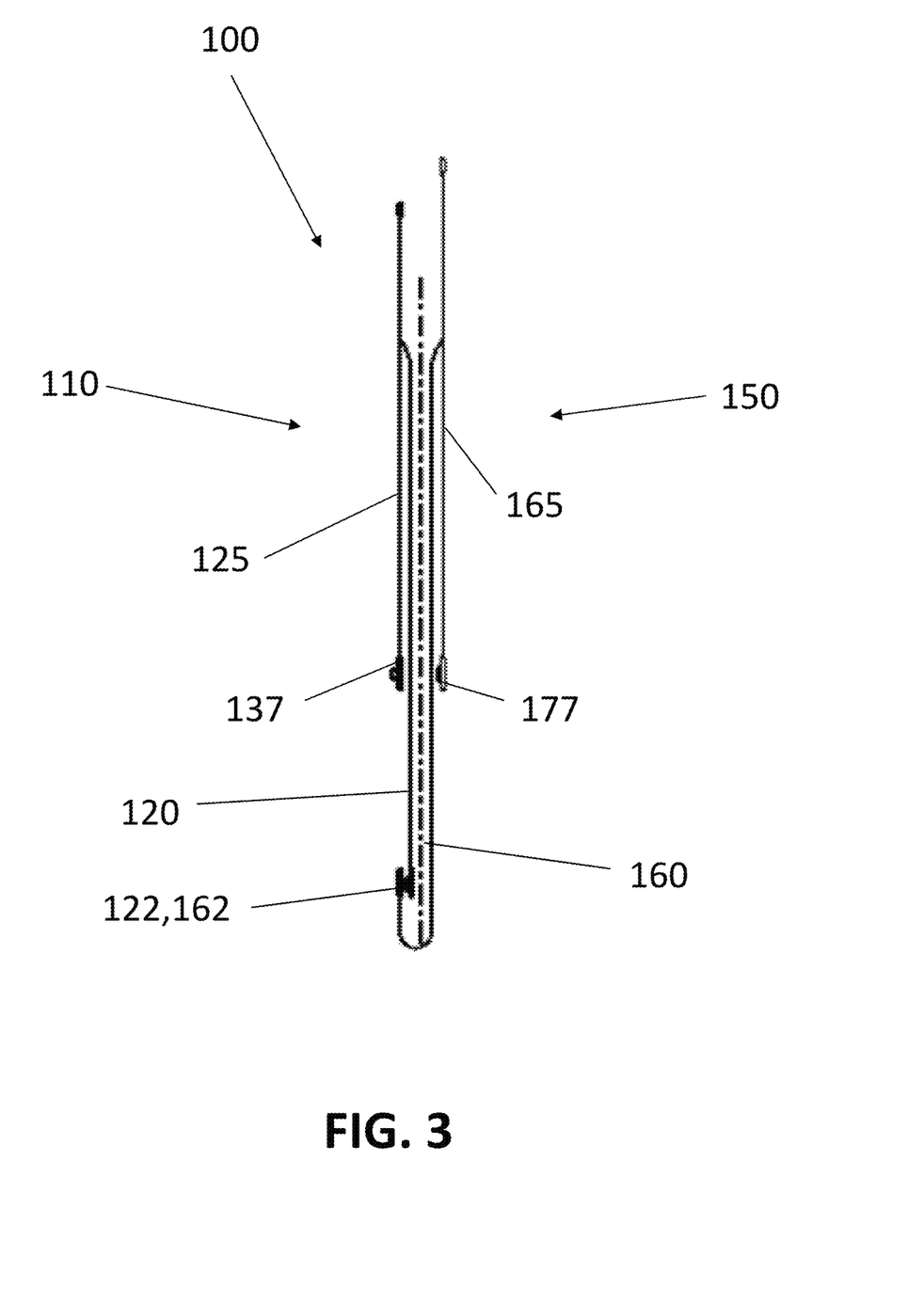
FIG. 3 illustrates a sectional view of an example arrangement of an arm immobilization apparatus.

FIG. 3 illustrates a sectional view of arm immobilization apparatus 100 taken about section 3-3 in FIG. 2. Arm immobilization apparatus 100 may have an anterior portion 110 and a posterior portion 150.

Anterior portion 110 may include anterior flap 125 having at least one fastening device 137. Anterior flap 125 may be affixed to anterior portion 110 at about the anterior of the torso of a patient (not shown). Anterior portion 110 may also include inferior portion 120 having at least one fastening device 122. Anterior flap 125 may be affixed, either integrally or removably, at about the anterior of the torso of a patient (not shown). Anterior flap 125 may be affixed at about the waist of a patient. Anterior flap 125 may be affixed at about the chest of a patient. Anterior flap 125 may be affixed at about the anterior torso, including at about the waist or chest of a patient, and may further be affixed under the arm of the patient. Anterior flap 125 may be affixed about a seam or a series of connection points that extend at least across a part of the patient's anterior torso (such as about the waist or chest) and under a patient's arm. The orientation and location of the affixation point of anterior flap 125 may be any orientation and location configured to cause anterior flap 125 to extend upwardly across at least a portion of the patient's arm so as to immobilize the patient's arm. The orientation and location of the affixation point of anterior flap 125 may be any orientation and location configured to cause anterior flap 125 to extend upwardly across at least a portion of the patient's arm and specifically at least the elbow and forearm of the patient, so as to immobilize the patient's arm.

Each of anterior flap 125 and posterior flap 165 may comprise a single flap member that extends over at least one of the left shoulder and the right shoulder. Both anterior flap 125 and posterior flap 165 may be configured to permit at least one fastening device 137 to be operatively connected to at least one fastening device 177 at a position superior to either, or both, of the patent's shoulders. Both anterior inferior portion 120 and posterior inferior portion 160 may be configured to permit at least one fastening device 122 to be operatively connected to at least one fastening device 162 at a position inferior to the pelvis of a patient.

Figure 4:
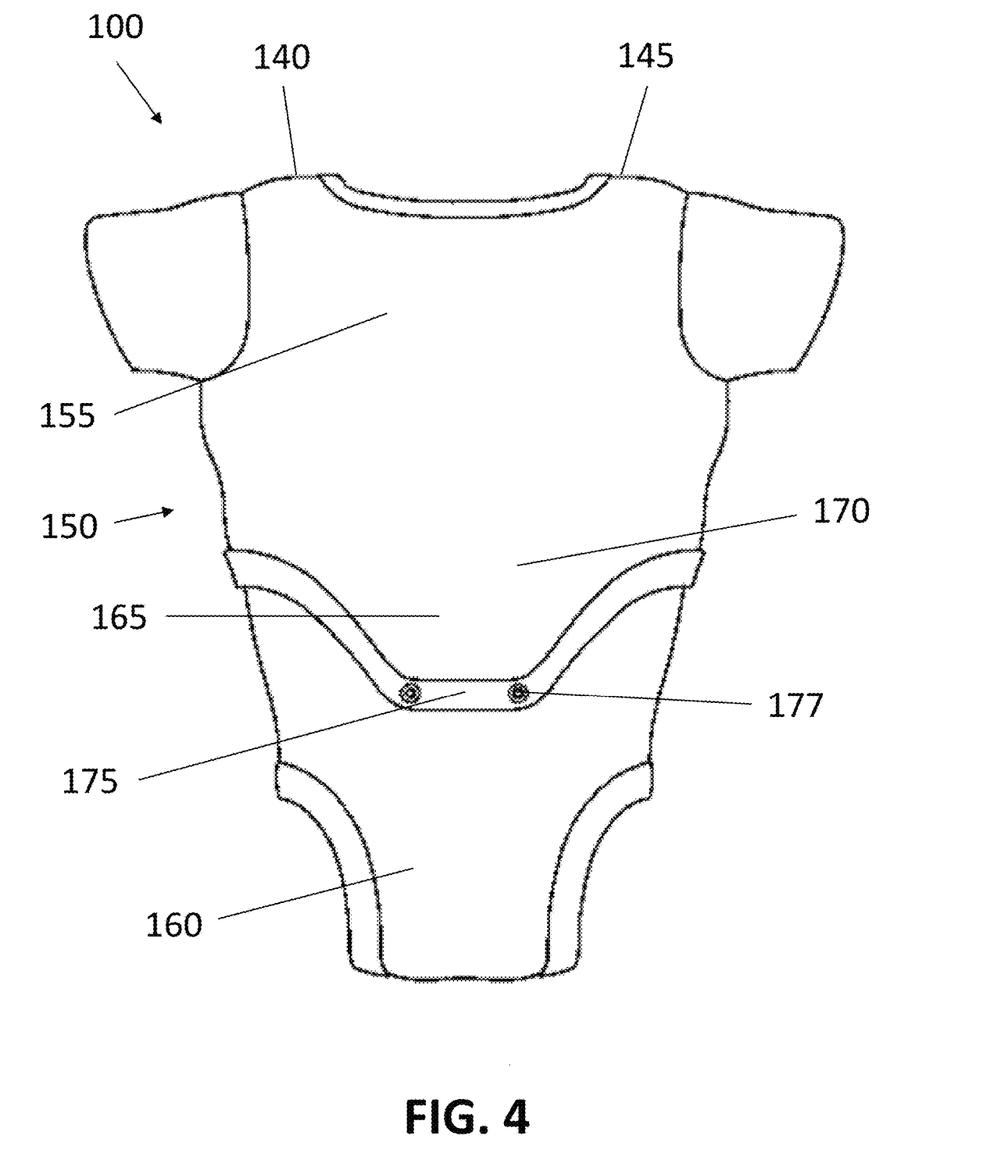
FIG. 4 illustrates a rear elevational view of an example arrangement of an arm immobilization apparatus.

FIG. 4 illustrates a rear elevational view of arm immobilization apparatus 100, which may include posterior portion 150 having a superior portion 155 and inferior portion 160.

Superior portion 155 and inferior portion 160 may be operatively connected. Superior portion 155 and inferior portion 160 may be integrally connected. Superior portion 155 and inferior portion 160 may be removably connected.

Posterior flap 165 may include proximal end 170 and a distal end 175. Proximal end 170 of posterior flap 165 may be affixed to posterior portion 150 at about the posterior torso of the patient.

Distal end 175 of posterior flap 165 may include at least one fastening device 177. Posterior flap 165 may be of sufficient length to permit distal end 175 of posterior flap 165 to be pulled over at least one of the shoulders of the patient. Posterior flap 165 may be of sufficient length to permit distal end 175 of posterior flap 165 to be pulled over both of the shoulders of the patient.

Anterior portion 110 may be joined to posterior portion 150 at one or more of the left side, right side, left shoulder, and right shoulder of the patient. Anterior portion 110 and posterior portion 150 may be integrally connected. Anterior portion 110 and posterior portion 150 may be removably connected.

At least one of anterior portion 110 and posterior portion 150 may cover at least a portion of the torso of the patient. Posterior inferior portion 160 may be of sufficient length to extend distally about the pelvis, or between a left leg and a right leg, of the patient and meet, overlap, or underlap, with at least a portion of anterior inferior portion 120.

At least one of anterior inferior portion 120 and posterior inferior portion 160 may include at least one fastening device 122, 162. At least one fastening device 122 of anterior inferior portion 120 may be operatively connected to at least one fastening device 162 of posterior inferior portion 160 when posterior inferior portion 160 is extended distally about the pelvis, or between the left leg and the right leg, of the patient and oriented to meet, overlap, or underlap, with at least a portion of anterior inferior portion 120. At least one fastening device 122, 162 may be configured to removably attach at least one of one another, anterior inferior portion 120, or posterior inferior portion 160.

At least one fastening device 137 of distal end 135 of anterior flap 125 may be configured to be operatively connected to at least one fastening device 177 of distal end 175 of posterior flap 165 at a position superior to at least one of the shoulders of the patient. At least one fastening device 137 of distal end 135 of anterior flap 125 may be configured to be operatively connected to at least one fastening device 177 of distal end 175 of posterior flap 165 at a position superior to both of the shoulders of the patient. At least one fastening device 137, 177 may be configured to removably attach at least one of one another, distal end 135, or distal end 175.

In one embodiment, a method for immobilizing an injured arm of a patient may include dressing a patient in an arm immobilization apparatus 100 having anterior portion 110 having superior portion 115 and inferior portion 120, and having posterior portion 150 having superior portion 155 and inferior portion 160. Anterior portion 110 may be joined to posterior portion 150 at one or more of the left side, right side, left shoulder, and right shoulder of the patient, wherein at least one of anterior portion 110 and posterior portion 150 may cover at least a portion of the torso of the patient. Posterior inferior portion 160 may be of sufficient length to extend distally about the pelvis of the patient and overlap or underlap with at least a portion of anterior inferior portion 120. At least one of anterior inferior portion 120 and posterior inferior portion 160 may include at least one fastening device 122, 162 configured to permit at least one fastening device 122 of anterior inferior portion 120 to be operatively connected to at least one fastening device 162 of posterior inferior portion 160 when posterior inferior portion 160 is extended distally about the pelvis of the patient and oriented to overlap or underlap with at least a portion of anterior inferior portion 120.

Anterior flap 125 may have proximal end 130 and distal end 135, wherein proximal end 130 of anterior flap 125 may be affixed to anterior portion 110 at about the anterior torso of the patient, wherein distal end 135 of anterior flap 125 may include at least one fastening device 127, wherein anterior flap 125 may be of sufficient length to permit distal end 135 of anterior flap 125 to be pulled over either shoulder of the patient. Anterior flap 125 may be configured to permit distal end 135 of anterior flap 125 to be pulled over both shoulders of the patient.

Posterior flap 165 may have proximal end 170 and distal end 175, wherein proximal end 170 of posterior flap 165 may be affixed to posterior portion 150 at about the posterior torso of the patient, wherein distal end 175 of posterior flap 165 may include at least one fastening device 177, wherein posterior flap 165 may be of sufficient length to permit distal end 175 of posterior flap 165 to be pulled over at least one of the shoulders of the patient, wherein the at least one fastening device 137 of distal end 135 of anterior flap 125 may be configured to be operatively connected to at least one fastening device 177 of distal end 175 of posterior flap 165 at a position superior to at least one of the shoulders of the patient. At least one fastening device 137 of distal end 135 of anterior flap 125 may be configured to be operatively connected to at least one fastening device 177 of distal end 175 of posterior flap 165 at a position superior to both of the shoulders of the patient.

Distal end 135 of anterior flap 125 may be extended toward the feet of the patient. Distal end 175 of posterior flap 165 may be extended toward the head of the patient. At least one fastening device 177 of distal end 175 of posterior flap 165 may be positioned superior and posterior to the shoulder of the arm to be immobilized. The upper portion of the arm to be immobilized may be placed at about the side of the patient, and the lower portion of the arm to be immobilized may be placed at an angle from the upper portion of the arm, wherein the arm of the patient may be flexed at the elbow at about 90°. and adducted across the torso of the patient. The arm of the patent may be immobilized at any angle capable in a human arm, including angles less than 90° and greater than 90°. Distal end 135 of anterior flap 125 may be oriented over the arm to be immobilized. Distal end 135 of anterior flap 125 may be extended toward the head of the patient, wherein at least one fastening device 137 of distal end 135 of 125 anterior flap may be positioned superior and anterior to the opposite shoulder of the arm to be immobilized. At least one fastening device 137 of distal end 135 of anterior flap 125 may be secured to at least one fastening device 177 of distal end 175 of posterior flap 165, wherein distal end 135 of anterior flap 125 may be operatively connected to distal end 175 of posterior flap 165 at a position superior to the opposite shoulder of the immobilized arm of the patient. Distal end 135 of anterior flap 125 may be operatively connected to distal end 175 of posterior flap 165 at a position superior to both of the shoulders of the patient. Distal end 135 of anterior flap 125 may be operatively connected to distal end 175 of posterior flap 165 at a position superior to the shoulder of the immobilized arm of the patient.

Other embodiments of the method for immobilizing an injured arm of a patient may include dressing a patient in any embodiment of an arm immobilization apparatus.

Figure 5:
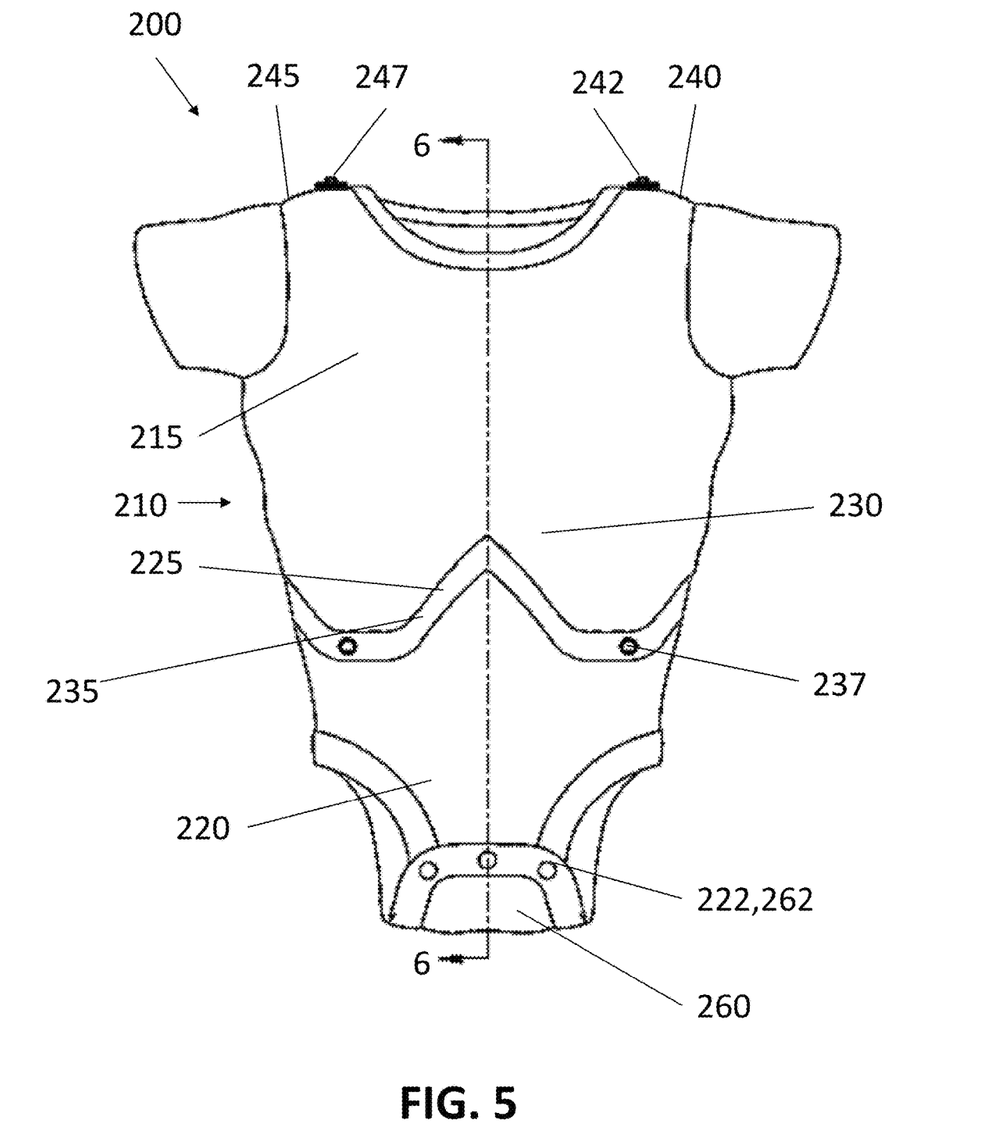
FIG. 5 illustrates a front elevational view of an example arrangement of an arm immobilization apparatus.

FIG. 5 illustrates a front elevational view of one example arrangement of an arm immobilization apparatus 200. Arm immobilization apparatus 200 may include an anterior portion 210 having a superior portion 215 and an inferior portion 220. Superior portion 215 may include an anterior flap 225.

Anterior flap 225 may include a proximal end 230 and a distal end 235. Proximal end 230 of anterior flap 225 may be affixed to anterior portion 210 at about the anterior torso of the patient. Distal end 235 of anterior flap 225 may include at least one fastening device 237.

Anterior flap 225 may be of sufficient length to permit distal end 235 of anterior flap 225 to be pulled over either shoulder of the patient. Anterior flap 225 may be configured to permit distal 235 end of anterior flap 225 to be pulled over both shoulders of the patient.

Arm immobilization apparatus 200 may include anterior portion 210 having superior portion 215 and inferior portion 220, and may include posterior portion 250 (not shown) having a superior portion 255 (not shown) and an inferior portion 260.

Anterior portion 210 may be integrally or removably joined to posterior portion 250 at one or more of the left side, right side, left shoulder, and right shoulder of the patient. At least one of anterior portion 210 and posterior portion 250 may cover at least a portion of the torso of the patient.

Posterior inferior portion 260 may be of sufficient length to extend distally about the pelvis, or between a left leg and a right leg, of the patient and overlap or underlap with at least a portion of anterior inferior portion 220. At least one of anterior inferior portion 220 and posterior inferior portion 260 may include at least one fastening device 222,262 configured to permit at least one fastening device 222 of anterior inferior portion 220 to be operatively connected to at least one fastening device 262 of posterior inferior portion 260 when posterior inferior portion 260 is extended distally about the pelvis, or between the left leg and the right leg, of the patient. Posterior inferior portion 260 may be oriented to meet, overlap, or underlap, with at least a portion of anterior inferior portion 220.

Arm immobilization apparatus 200 may include left shoulder portion 240 and right shoulder portion 245. At least one of left shoulder portion 240 and right shoulder portion 245 may include at least one fastening device 242,247.

Anterior flap 225 may include proximal end 230 and distal end 235, and proximal end 230 of anterior flap 225 may be affixed to anterior portion 210 at about the anterior torso of the patient. Distal end 235 of anterior flap 225 may include at least one fastening device 237. Anterior flap 225 may be of sufficient length to permit distal end 235 of anterior flap 225 to be pulled over at least one of the shoulders of the patient. At least one fastening device 237 of distal end 235 of anterior flap 225 may be configured to be operatively connected to at least one fastening device 242, 247 of at least one of left shoulder portion 240 and right shoulder portion 245. Anterior flap 225 may be configured to permit at least one fastening device 237 to be operatively connected to at least one fastening device 242, while simultaneously permitting at least one fastening device 237 to be operatively connected to at least one fastening device 247.

Figure 6:
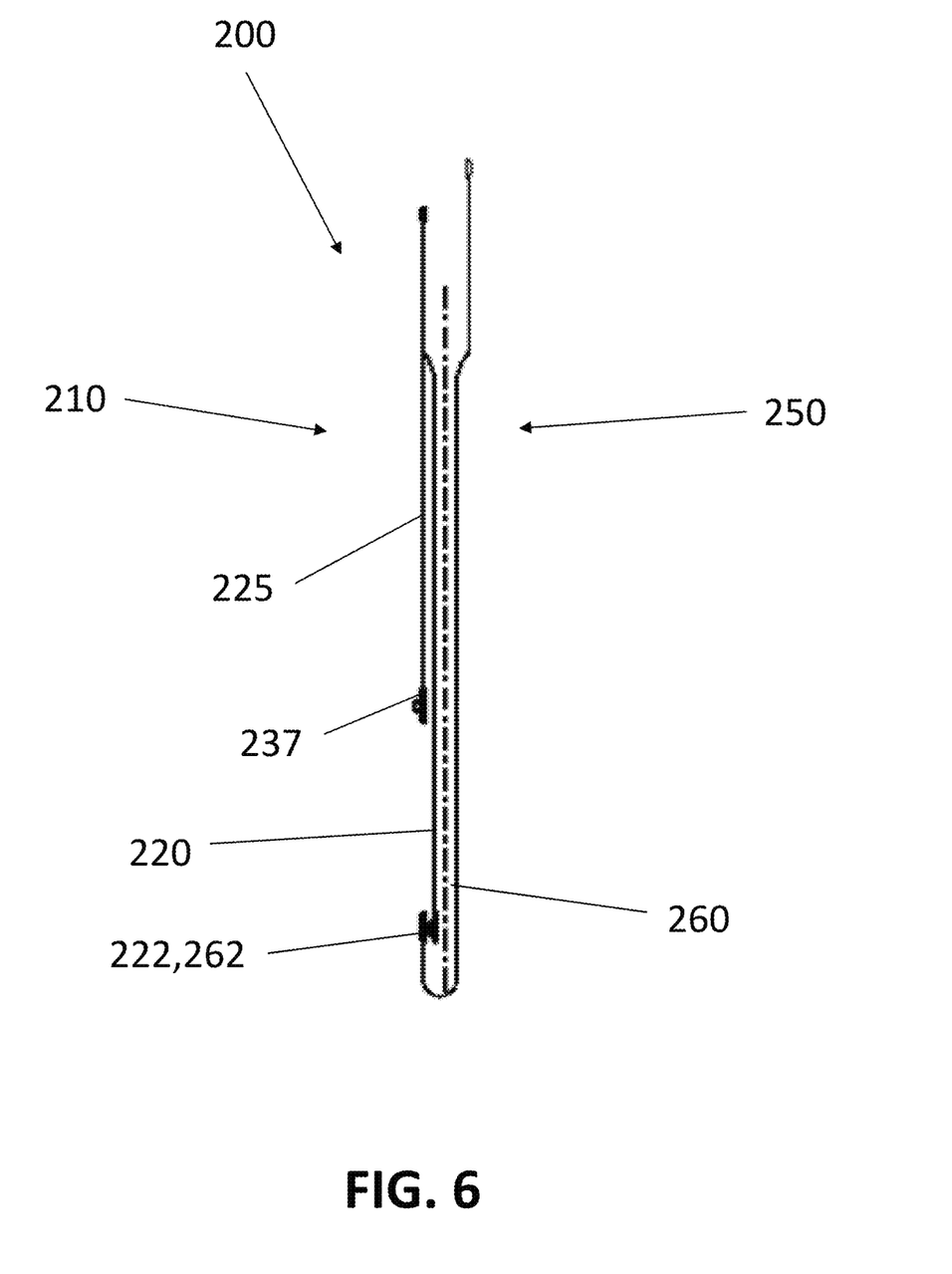
FIG. 6 illustrates a sectional view of an example arrangement of an arm immobilization apparatus.

FIG. 6 illustrates a sectional view of one example arrangement of arm immobilization apparatus 200 taken about section 6-6 in FIG. 5. Arm immobilization apparatus 200 may include anterior portion 210 and posterior portion 250. Anterior portion 210 may include anterior flap 225 having at least one fastening device 237. Anterior flap 225 may be affixed to anterior portion 210 at about the anterior of the torso of a patient (not shown). Anterior portion 210 may also include inferior portion 220 having at least one fastening device 222. Posterior portion 250 may include inferior portion 260 having at least one fastening device 262.

Anterior flap 225 may be affixed, either integrally or removably, at about anterior portion 210. Anterior flap 225 may be affixed at about the waist of a patient. Anterior flap 225 may be affixed at about the chest of a patient. Anterior flap 225 may be affixed at about anterior portion 210, including at about the waist or chest of a patient, and may further be affixed under the arm of the patient. Anterior flap 225 may be affixed about a seam or a series of connection points that extend at least across a part of the patient's anterior portion 210 (such as about the waist or chest) and under a patient's arm. The orientation and location of the affixation point of anterior flap 225 may be any orientation and location configured to cause anterior flap 225 to extend upwardly across at least a portion of the patient's arm so as to immobilize the patient's arm. The orientation and location of the affixation point of anterior flap 225 may be any orientation and location configured to cause anterior flap 225 to extend upwardly across at least a portion of the patient's arm and specifically at least the elbow and forearm of the patient, so as to immobilize the patient's arm.

Anterior flap 225 may be configured to permit at least one fastening device 237 to be operatively connected to at least one fastening device (not shown) at a position superior to either of the patent's shoulders. Anterior flap 225 may be configured to permit at least one fastening device 237 to be operatively connected to at least one fastening device (not shown) at a position superior to at least one of the patent's shoulders.

Anterior inferior portion 220 and posterior inferior portion 260 may be configured to permit at least one fastening device 222 to be operatively connected to at least one fastening device 262 at a position inferior to the pelvis of a patient.

Figure 7:
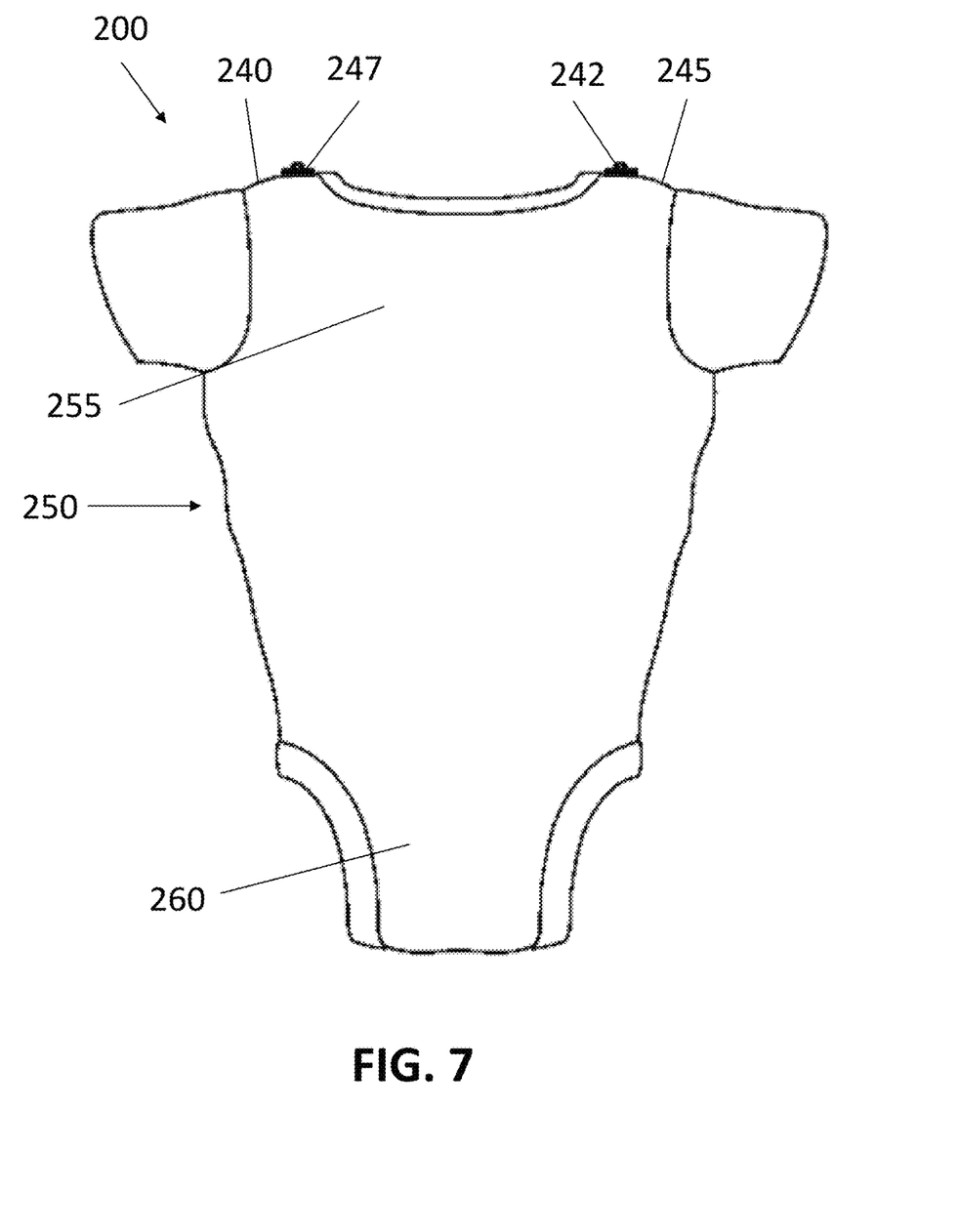
FIG. 7 illustrates a rear elevational view of an example arrangement of an arm immobilization apparatus.

FIG. 7 illustrates a rear elevational view of one example arrangement of arm immobilization apparatus 200, which may include posterior portion 250 having superior portion 255 and inferior portion 260.

Anterior portion 210 may be integrally or removably joined to posterior portion 250 at one or more of the left side, right side, left shoulder, and right shoulder of the patient. At least one of anterior portion 210 and posterior portion 250 may cover at least a portion of the torso of the patient.

Posterior inferior portion 260 may be of sufficient length to extend distally about the pelvis of the patient and meet, overlap, or underlap, with at least a portion of anterior inferior portion 220. At least one of anterior inferior portion 220 and posterior inferior portion 260 may include at least one fastening device 222,262 configured to permit at least one fastening device 222 of anterior inferior portion 220 to be operatively connected to at least one fastening device 262 of posterior inferior portion 260 when posterior inferior portion 260 is extended distally about the pelvis, or between the left leg and the right leg, of the patient and oriented to meet, overlap, or underlap, with at least a portion of anterior inferior portion 220.

At least one fastening device 237 of distal end 235 of anterior flap 225 may be configured to be operatively connected to the at least one fastening device 242,247 of left shoulder portion 240 and/or right shoulder portion 245, respectively, at a position superior to at least one of the shoulders of the patient. At least one fastening device 237 of distal end 235 of anterior flap 225 may be operatively connected to the at least one fastening device 242,247 of left shoulder portion 240 and right shoulder portion 245, respectively, at a position superior to both of the shoulders of the patient.

Any of the fastening devices described herein may be at least one of a fastening device from a group consisting of a snap, a tie, a hook and loop fastener, a button, a hole, a zipper, an adhesive, a magnet, a clasp, a pin, a safety pin, a hook, a frog, a toggle, a drawstring, a lace, a stud, an eyelet, a rivet, a socket, a grommet, a clip, a strap, a buckle, a slide, a chain, a clamp, a ring, a cord, and a bar.

Any of the fastening devices described herein may be singular devices (e.g., one fastening device at each stated location), or a plurality of devices. Fastening devices described herein, such as for example fastening device 177, or 242, may include a single fastening device or a plurality of fastening devices. Fastening devices may include a pair of fastening devices oriented adjacent or near one another so as to spread the force of the fastened articles about the pair of fastening devices. Fastening devices may include two or more fastening devices oriented adjacent or near one another so as to spread the force of the fastened articles about the pair of fastening devices.

In one embodiment, at least one of anterior flap 125, posterior flap 165, anterior flap 225, left shoulder portion 240, and right shoulder portion 245 may be reinforced with a reinforcement material. At least one of anterior flap 125, posterior flap 165, anterior flap 225, left shoulder portion 240, and right shoulder portion 245 may be reinforced to avoid stretching. At least one of anterior flap 125, posterior flap 165, anterior flap 225, left shoulder portion 240, and right shoulder portion 245 may be reinforced to avoid tearing or any other failure. At least one of anterior flap 125, posterior flap 165, anterior flap 225, left shoulder portion 240, and right shoulder portion 245 may be reinforced with a reinforcement material, including, for example, a mesh, cordage, straps, an additional layer of material, a substrate, and the like.

In one embodiment, at least one of left shoulder portion 140, right shoulder portion 145, left shoulder portion 240, and right shoulder portion 245 may include a padding material. The padding material may be configured to at least one of: reduce pressure on the patient's shoulder, spread force over a patient's shoulder, reduce chafing, reduce bunching, reduce strain of the material, reduce pinching of the patient's shoulder or neck, reduce abrasion of the patient's shoulder or neck, and the like.

In one embodiment, at least one of anterior flap 125, posterior flap 165, posterior portion 150, and posterior portion 250 may include additional fastening devices oriented to fasten at least one of anterior flap 125, posterior flap 165, posterior portion 150, and posterior portion 250 under a patient's arm. The fastening devices oriented under the patient's arm may be in addition to those described above extending superior to the patient's shoulder. The fastening devices oriented under the patient's arm may act to further immobilize the patient's arm. The fastening devices oriented under the patient's arm may act to spread force from the patient's shoulder.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to take into consideration the degree of precision available or prudent in manufacturing. To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The invention claimed is:

1. An apparatus A garment for immobilizing an injured arm of a patient, comprising:
   an anterior portion having an inferior portion and a superior portion;
   a posterior portion having an inferior portion and a superior portion;
   wherein the anterior portion is joined to the posterior portion at the left side, right side, left shoulder, and right shoulder of the patient,
   wherein at least one of the anterior portion and the posterior portion covers a substantial portion of the torso of the patient,
   wherein the posterior inferior portion is of sufficient length to extend distally between a left leg and a right leg of the patient and overlap or underlap with at least a portion of the anterior inferior portion,
   wherein at least one of the anterior inferior portion and the posterior inferior portion includes at least one fastening device,
   an anterior flap having a proximal end and a distal end,
   wherein the proximal end of the anterior flap is attached to the anterior portion between the inferior portion and the superior portion,
   wherein the distal end of the anterior flap includes at least one fastening device,
   wherein the anterior flap is of sufficient length to permit the distal end of the anterior flap to be pulled over at least one shoulder of the patient;
   a posterior flap having a proximal end and a distal end,
   wherein the proximal end of the posterior flap is attached to the posterior portion between the inferior portion and the superior portion,
   wherein the distal end of the posterior flap includes at least one fastening device,
   wherein the posterior flap is of sufficient length to permit the distal end of the posterior flap to be pulled over at least one shoulder of the patient,
   wherein the at least one fastening device of the distal end of the anterior flap is configured to be operatively connected to the at least one fastening device of the distal end of the posterior flap at a position superior to one of the left shoulder and the right shoulder of the patient,
   wherein the anterior flap and the posterior flap each comprise a single flap member that extends over at least one of the left shoulder and the right shoulder, and
   wherein the anterior flap and the posterior flap together immobilize the injured arm of the patient.

2. The garment of claim 1, wherein each of the anterior inferior portion and the posterior inferior portion includes at least one fastening device, and wherein the at least one fastening device is configured to permit the at least one fastening device of the anterior inferior portion to be operatively connected to the at least one fastening device of the posterior inferior portion when the posterior inferior portion is extended distally between a left leg and a right leg of the patient and oriented to meet, overlap, or underlap with at least a portion of the anterior inferior portion.

3. The garment of claim 1, wherein the distal end of the anterior flap and the distal end of the posterior flap are each configured to be operatively connected over both shoulders of the patient.

4. The garment of claim 1, wherein the at least one fastening device is at least one of: a snap, a tie, a hook and loop fastener, a button, a hole, a zipper, an adhesive, a magnet, a clasp, a pin, a safety pin, a hook, a frog, a toggle, a drawstring, a lace, a stud, an eyelet, a rivet, a socket, a grommet, a clip, a strap, a buckle, a slide, a chain, a clamp, a ring, a cord, and a bar.

5. The garment of claim 1, wherein the at least one fastening device is a snap.

6. A garment for immobilizing an injured arm of a patient, comprising:
   an anterior portion having an inferior portion and a superior portion;
   a posterior portion having an inferior portion and a superior portion;
   wherein the anterior portion is joined to the posterior portion at the left side, right side, left shoulder, and right shoulder of the patient,
   wherein at least one of the anterior portion and the posterior portion covers a substantial portion of the torso of the patient,
   wherein the posterior inferior portion is of sufficient length to extend distally between a left leg and a right leg of the patient and overlap or underlap with at least a portion of the anterior inferior portion,
   wherein at least one of the anterior inferior portion and the posterior inferior portion includes at least one fastening device,
   an anterior flap having a proximal end and a distal end,
   wherein the proximal end of the anterior flap is attached to the anterior portion between the inferior portion and the superior portion,
   wherein the distal end of the anterior flap includes at least one fastening device,
   wherein the anterior flap is of sufficient length to permit the distal end of the anterior flap to be pulled over at least one shoulder of the patient;
   a posterior flap having a proximal end and a distal end,
   wherein the proximal end of the posterior flap is attached to the posterior portion between the inferior portion and the superior portion,
   wherein the distal end of the posterior flap includes at least one fastening device,
   wherein the posterior flap is of sufficient length to permit the distal end of the posterior flap to be pulled over at least one shoulder of the patient, and
   wherein the anterior flap and the posterior flap together immobilize the injured arm of the patient.

7. The garment of claim 6, wherein each of the anterior inferior portion and the posterior inferior portion includes at least one fastening device, and wherein the at least one fastening device is configured to permit the at least one fastening device of the anterior inferior portion to be operatively connected to the at least one fastening device of the posterior inferior portion when the posterior inferior portion is extended distally between a left leg and a right leg of the pelvis of the patient and oriented to meet, overlap, or underlap with at least a portion of the anterior inferior portion.

8. The garment of claim 6, wherein the distal end of the anterior flap and the distal end of the posterior flap are each configured to be operatively connected over both shoulders of the patient.

9. The garment of claim 6, wherein the at least one fastening device is at least one of: a snap, a tie, a hook and loop fastener, a button, a hole, a zipper, an adhesive, a magnet, a clasp, a pin, a safety pin, a hook, a frog, a toggle, a drawstring, a lace, a stud, an eyelet, a rivet, a socket, a grommet, a clip, a strap, a buckle, a slide, a chain, a clamp, a ring, a cord, and a bar.

10. The garment of claim 6, wherein the at least one fastening device is a snap.

11. A garment for immobilizing an injured arm of a patient, comprising:
 an anterior portion having an inferior portion and a superior portion;
 a posterior portion having an inferior portion and a superior portion;
 wherein the anterior portion is joined to the posterior portion at the left side, right side, left shoulder, and right shoulder of the patient,
 wherein at least one of the anterior portion and the posterior portion covers a substantial portion of the torso of the patient,
 wherein the posterior inferior portion is of sufficient length to extend distally about the pelvis of the patient and overlap or underlap with at least a portion of the anterior inferior portion,
 wherein at least one of the anterior inferior portion and the posterior inferior portion includes at least one fastening device,
 an anterior flap having a proximal end and a distal end,
 wherein the proximal end of the anterior flap is attached to the anterior portion between the inferior portion and the superior portion,
 wherein the distal end of the anterior flap includes at least one fastening device,
 wherein the anterior flap is of sufficient length to permit the distal end of the anterior flap to be pulled over at least one shoulder of the patient;
 a posterior flap having a proximal end and a distal end,
 wherein the proximal end of the posterior flap is attached to the posterior portion between the inferior portion and the superior portion,
 wherein the distal end of the posterior flap includes at least one fastening device,
 wherein the posterior flap is of sufficient length to permit the distal end of the posterior flap to be pulled over at least one shoulder of the patient,
 wherein the at least one fastening device of the distal end of the anterior flap is configured to be operatively connected to the at least one fastening device of the distal end of the posterior flap at a position superior to one of the left shoulder and the right shoulder of the patient, and
 wherein the anterior flap and the posterior flap together immobilize the injured arm of the patient.

12. The garment of claim 11, wherein each of the anterior inferior portion and the posterior inferior portion includes at least one fastening device, and wherein the at least one fastening device is configured to permit the at least one fastening device of the anterior inferior portion to be operatively connected to the at least one fastening device of the posterior inferior portion when the posterior inferior portion is extended distally about the pelvis of the patient and oriented to meet, overlap, or underlap with at least a portion of the anterior inferior portion.

13. The garment of claim 11, wherein the distal end of the anterior flap and the distal end of the posterior flap are each configured to be operatively connected over both shoulders of the patient.

14. The garment of claim 11, wherein the at least one fastening device is at least one of: a snap, a tie, a hook and loop fastener, a button, a hole, a zipper, an adhesive, a magnet, a clasp, a pin, a safety pin, a hook, a frog, a toggle, a drawstring, a lace, a stud, an eyelet, a rivet, a socket, a grommet, a clip, a strap, a buckle, a slide, a chain, a clamp, a ring, a cord, and a bar.

15. The garment of claim 11, wherein the at least one fastening device is a snap.

* * * * *